(12) United States Patent
Rudenko et al.

(10) Patent No.: US 10,370,320 B2
(45) Date of Patent: Aug. 6, 2019

(54) PURIFICATION METHODS

(71) Applicant: Rohm and Haas Electronic Materials LLC, Marlborough, MA (US)

(72) Inventors: Andrey Rudenko, Clinton, MA (US); Gerhard Pohlers, Needham, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 16/221,881

(22) Filed: Dec. 17, 2018

(65) Prior Publication Data

US 2019/0202767 A1  Jul. 4, 2019

Related U.S. Application Data

(60) Provisional application No. 62/612,436, filed on Dec. 30, 2017.

(51) Int. Cl.
| | | |
|---|---|---|
| *C07C 51/44* | (2006.01) | |
| *C07C 7/20* | (2006.01) | |
| *C11C 3/10* | (2006.01) | |
| *C07D 307/08* | (2006.01) | |
| *C11C 1/10* | (2006.01) | |

(52) U.S. Cl.
CPC .............. *C07C 51/44* (2013.01); *C07C 7/20* (2013.01); *C07D 307/08* (2013.01); *C11C 1/103* (2013.01); *C11C 3/10* (2013.01)

(58) Field of Classification Search
None
See application file for complete search history.

(56) References Cited

U.S. PATENT DOCUMENTS

| | | |
|---|---|---|
| 2,407,861 A | 9/1946 | Wolk |
| 2,485,070 A | 10/1949 | Schulze et al. |
| 3,221,030 A | 11/1965 | Huffman |
| 7,560,579 B2 | 7/2009 | Te Baay et al. |
| 9,388,107 B2 * | 7/2016 | Martens ................ C07C 45/006 |

* cited by examiner

*Primary Examiner* — Tam M Nguyen
(74) *Attorney, Agent, or Firm* — Jonathan D. Baskin

(57) ABSTRACT

Provided are purification methods, comprising: (a) providing an organic solvent and a phenolic peroxide formation inhibitor, wherein the organic solvent has a first boiling point at standard atmospheric pressure ($bp_1$) and the phenolic peroxide formation inhibitor has a second boiling point at standard atmospheric pressure ($bp_2$) that satisfy the following inequality (I):

$$bp_2 \leq (1.10)(bp_1) \qquad (I); \text{ and}$$

(b) heating the organic solvent and the phenolic peroxide formation inhibitor to a temperature causing the organic solvent and phenolic peroxide formation inhibitor to vaporize, and (ii) condensing the vaporized organic solvent and peroxide formation inhibitor to provide a purified mixture of the organic solvent and peroxide formation inhibitor. The methods find particular use in the purification of solvents that are useful in process chemicals for the manufacture of semiconductor devices.

10 Claims, 1 Drawing Sheet

PURIFICATION METHODS

This application claims the benefit of priority under 35 U.S.C. § 119(e) to U.S. Provisional Application No. 62/612,436, filed Dec. 30, 2017, the entire contents of which are incorporated herein by reference.

BACKGROUND OF THE INVENTION

The invention relates generally to chemical purification. More specifically, this invention relates to the co-purification of an organic solvent and peroxide formation inhibitor to form a purified solvent mixture. The invention finds particular applicability in the preparation of solvent mixtures useful in the electronics industry.

In the semiconductor manufacturing industry, process materials used in device fabrication and their associated raw materials may be subject to contamination by peroxides such as organic peroxides. Organic solvents such as ethers and esters are particularly susceptible to organic peroxide formation in the presence of atmospheric oxygen. Among the susceptible organic solvents are ethyl lactate, propylene glycol monomethyl ether, dipropylene glycol monomethyl ether, and propylene glycol monomethyl ether acetate, which are commonly used in lithographic materials. Peroxide formation in these solvents may occur during storage of the solvents or compositions containing the solvents. The presence of peroxides in lithographic materials can adversely impact the patterns being formed, for example, their thicknesses or critical dimensions. This can result in defects and yield loss in the semiconductor devices being formed. The presence of peroxides in semiconductor process chemicals can further be problematic from a safety standpoint. In particular, peroxides can pose severe fire and explosion hazards and, moreover, can be toxic and corrosive. It therefore would be desirable to minimize or eliminate the formation of peroxides in organic solvents.

In an effort to minimize the formation of peroxides in organic solvents, the addition of peroxide formation inhibitors to purified organic solvents has been proposed, for example, in U.S. Pat. No. 3,221,030. Industrial inhibitors, however, contain metallic and/or high-boiling impurities which contaminate the pure solvent. Such impurities can adversely impact semiconductor manufacturing processes and resulting electronic devices, particularly in the case of advanced semiconductor devices wherein impurity reduction is of increased importance. Methods to stabilize peroxide-forming solvents while minimizing or avoiding metallic and/or high-boiling contaminants would therefore be desired.

Accordingly, there is a need in the art for improved purification methods which address one or more problems associated with the state of the art.

SUMMARY OF THE INVENTION

In accordance with one aspect of the invention, purification methods are provided. The purification methods comprise: (a) providing an organic solvent and a phenolic peroxide formation inhibitor, wherein the organic solvent has a first boiling point at standard atmospheric pressure ($bp_1$) and the phenolic peroxide formation inhibitor has a second boiling point at standard atmospheric pressure ($bp_2$) that satisfy the following inequality (I):

$$bp_2 \leq (1.10)(bp_1) \qquad \text{(I); and}$$

(b) heating the organic solvent and the phenolic peroxide formation inhibitor to a temperature causing the organic solvent and phenolic peroxide formation inhibitor to vaporize, and (ii) condensing the vaporized organic solvent and phenolic peroxide formation inhibitor to provide a purified mixture of the organic solvent and phenolic peroxide formation inhibitor.

BRIEF DESCRIPTION OF THE DRAWINGS

The present invention will be described with reference to the following drawings, in which.

DETAILED DESCRIPTION

Figure 1:
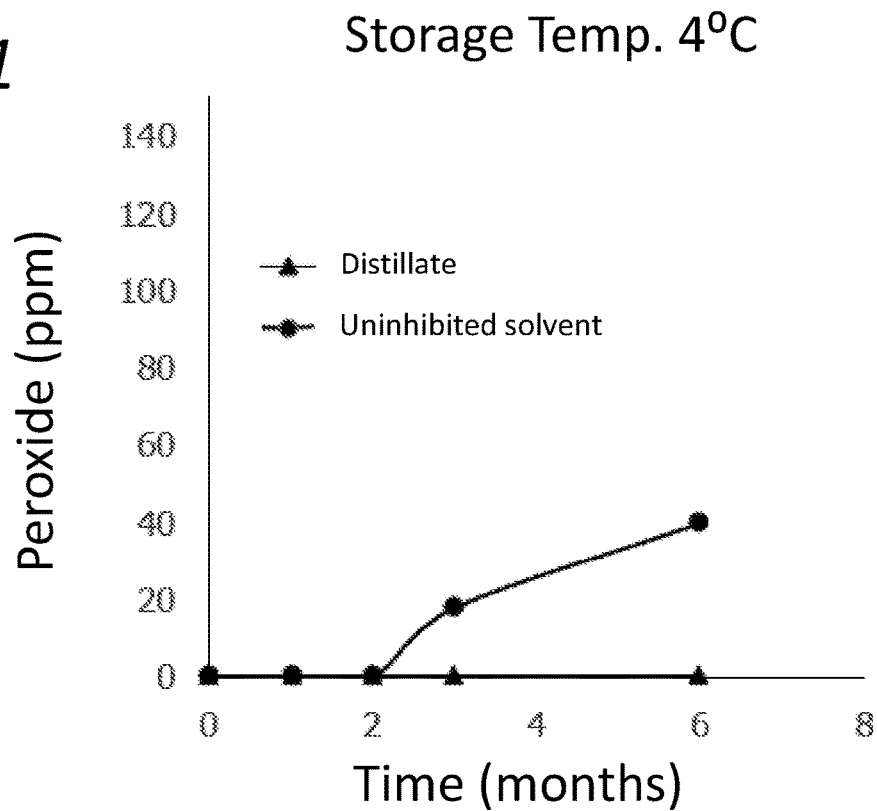
FIG. 1 is a graph showing peroxide content as a function of time at 4° C. for peroxide-inhibited solvent purified in accordance with the invention and for a comparative uninhibited solvent.

In order to solve one or more problems associated with the state of the art, new purification methods have been developed by which an organic solvent and a phenolic peroxide formation inhibitor can be simultaneously processed to form a purified mixture of those components. The methods of the invention have particular applicability to the electronics industry.

One or more organic solvents may be treated together in the methods of the invention. Suitable organic solvents include, for example: ethers such as isoamyl ether, methyl tert-butyl ether, tetrahydrofuran, 2-butoxyethanol, propylene glycol monomethyl ether (PGME), dipropylene glycol monomethyl ether (DPM), dipropylene glycol dimethyl ether, and tripropylene glycol monomethyl ether (TPM); esters such as ethyl-3-ethoxy propionate, ethyl lactate, and propylene glycol monomethyl ether acetate (PGMEA); alcohols such as isopropyl alcohol, methyl isobutyl carbinol (MIBC), propylene glycol, dipropylene glycol, and tripropylene glycol; aromatics such as diisopropyl benzene and triisopropyl benzene; and ketones such as acetone, cyclopentanone, and cyclohexanone; and combinations thereof. The solvent is typically chosen from ethers and esters.

Selection of an appropriate peroxide formation inhibitor will depend on the particular solvent being purified. The inhibitor should be soluble in the solvent. Suitable phenolic peroxide formation inhibitors include non-fluorinated or fluorinated phenols, for example, phenol, 2-methylphenol, 2-(trifluoromethyl)phenol, 4-methoxyphenol, 2,4-dimethyl-6-tert-butylphenol, 2,4-di(trifluoromethyl)-6-tert-butylphenol, 2,6-di-tert-butylphenol, 4-tert-butylpyrocatechol, and combinations thereof. Of these, 2-methylphenol, 2,4-dimethyl-6-tert-butylphenol, and combinations thereof, are typical. Typically, the peroxide formation inhibitor is used in an amount of from 1 to 1000 ppm, preferably from 10 to 100 ppm, based on the total inhibitor and solvent. Preferably, the content of the peroxide formation inhibitor in the purified solvent-inhibitor product will be approximately of the same ratio as the pre-purified components, although that will depend, for example, on the relative boiling points of the components and on purification process conditions.

Appropriate solvent-inhibitor pairings will depend, for example, on the relative boiling points of the solvent and inhibitor. The solvent has a first boiling point at standard atmospheric pressure ($bp_1$) and the peroxide formation inhibitor has a second boiling point at standard atmospheric pressure (bp$_2$) that satisfies the following inequality (I):

$$bp_2 \leq (1.10)(bp_1) \tag{I}$$

or more preferably that satisfies the following inequality (II):

$$(0.90)(bp_1) < bp_2 < (1.10)(bp_1) \tag{II}$$

or still more preferably that satisfies the following inequality (III):

$$(0.95)(bp_1) < bp_2 < (1.05)(bp_1) \tag{III}$$

When satisfying these inequalities, sufficient content of the peroxide formation inhibitor may be obtained in the purified mixture when using purification conditions that are typical for the solvent alone, based on amounts used of the pre-purified components. Both solvent and inhibitor can thereby be purified simultaneously. Preferably, the boiling point of the peroxide formation inhibitor bp$_2$ is less than that of the solvent bp$_1$.

Particularly suitable solvent/inhibitor combinations include, for example, 2-butoxyethanol/phenol, isoamyl ether/phenol; dipropyleneglycol dimethyl ether/phenol, propylene glycol/2-methylphenol, dipropylene glycol monomethyl ether/2-methylphenol, diisopropyl benzene/2-methylphenol, triisopropyl benzene/4-methoxyphenol, tripropylene glycol monomethyl ether/2,4-dimethyl-6-tert-butylphenol (Topanol A), cyclopentanone/2,6-di-tert-butylphenol, and tripropylene glycol/4-tert-butylpyrocatechol.

The solvent-inhibitor mixture is purified by a thermal purification process such as a distillation and/or fractionation process. The thermal purification process comprises heating the solvent-inhibitor mixture to a temperature effective to boil the mixture. A suitable temperature for the process will depend, for example, on the boiling points of the solvent and peroxide formation inhibitor, and the pressure under which the process is undertaken. Suitable temperatures can readily be determined based on pressure-temperature curves for the components.

The thermal purification process can be conducted at standard pressure (760 Torr) or, more preferably, at reduced pressure. Preferably, the thermal purification process is conducted by applying vacuum and heat to the solvent-inhibitor mixture. The application of vacuum allows for lower temperatures than would otherwise be required in such processes undertaken at standard pressure. Purification under vacuum is further advantageous in that it reduces the likelihood of formation of undesired side reactant impurities in the recovery process. A suitable pressure for the process will depend, for example, on vapor pressure of the solvent-inhibitor mixture and partial pressure of the components. A typical reduced pressure purification process may, for example, be carried at a pressure of from 0.01 to 50 Torr.

Distillation by exposing the solvent-inhibitor mixture to elevated temperature for relatively short times is also advantageous for reducing the likelihood of formation of undesired side reactant impurities in the recovery process. It may be desired, for example, to carry out the distillation step for a time less than five minutes, for a time less than three minutes, or for a time less than two minutes.

The thermal purification step can be carried out by short residence time distillation techniques. Suitable such techniques include, for example, wiped film evaporation, rising film evaporation, thin film evaporation, (centrifugal) molecular distillation, falling film distillation, or combinations thereof. Suitable such processes and tools for such processes are well known and disclosed, for example, in U.S. Pat. No. 7,560,579 B2.

In accordance with methods of the invention, the solvent and peroxide formation inhibitor can be pre-mixed prior to introduction into the thermal purification tool. The mixture can be prepared by adding the inhibitor to the solvent component. The mixture is then typically stirred or otherwise agitated to form a homogeneous mixture. Alternatively, the solvent and inhibitor can be separately introduced into the thermal purification tool.

The following non-limiting examples are illustrative of the invention.

EXAMPLES

Example 1

195 g of Dowanol™ TPM glycol ether (The Dow Chemical Company) and 0.002 g of Topanol™ A inhibitor (2,4-dimethyl-6-tert-butylphenol, TCI America) were combined in a plastic beaker and stirred to ensure mixing. 100 g of the resulting mixture was fed into a short path wiped film evaporator and distillation was carried out. The evaporator included a UIC-GmbH Short Path Distillation Unit, an IKA RW 20 Digital motor for the wiping blades and a Vacuubrand GMBH RZ2.5 Rotary vane pump. The mixture was fed from the top of the evaporator at a rate of 10-12 g/minute. The evaporator, with a total surface area of 0.02 m$^2$, was a jacketed borosilicate glass cylinder using hot oil to control temperature. Inside the heated surface, Teflon rollers were used to distribute the feed material. The residence time or contact time of the feed material to the heated surface was approximately 30-60 seconds. An internal condenser located in the center of the heated surface was used to condense the distillate phase which was collected in a receiver flask from an upper region of the evaporator. The non-volatile bottoms were collected in a separate receiver flask from a bottom region of the evaporator. The feed rate was controlled by a peristaltic pump. The jacket temperature was initially set to 40° C. until some bottoms were collected, and the temperature was then changed to 60° C. with subsequent adjustment, typically from 50-56° C. at steady-state, to control distillation split. Pressure of the evaporator at steady-state was approximately 100 mTorr. The steady-state process conditions were designed to attain a target split of 95-98% overhead. The overhead sample was collected in the receiver flask. The pre-distillation sample and post-distillation sample were analyzed for content of the Topanol A inhibitor. 9.1 g Topanol A inhibitor was observed in both the pre- and post-distillation samples.

Example 2

200 g of Dowanol™ DPM glycol ether (The Dow Chemical Company) and 0.002 g of 2-methylphenol inhibitor were combined in a plastic beaker and stirred to ensure mixing. Distillation of 100 g of the resulting mixture was performed using the procedure of Example 1, with the following differences:
  Feed Rate: 10-12 grams/minute
  Evaporator pressure: 3.5 Torr at steady-state
  Jacket Temperature: 45° C. initially with gradual increase to 50° C. through the distillation.
The pre-distillation sample and post-distillation sample were analyzed for content of the o-Cresol inhibitor. Inhibitor content of the pre-distillation sample was 20.2 ppm, and the post-distillation sample content was 10.7 ppm.

Example 3

20 L of Dowanol™ TPM glycol ether (The Dow Chemical Company) and 10 ppm of Topanol A inhibitor (TCI America) were combined in a round-bottom flask and stirred to ensure mixing. Distillation of the resulting mixture was performed using short path vacuum distillation. The individual pre-distillation TPM glycol ether and inhibitor, and the resulting distillate were analyzed for content of metal impurities using an Agilent 8800 ICP Mass Spectroscopy system. The data is summarized in Table 1, with metals content being provided in parts-per-billion (ppb).

TABLE 1

|    | Pre-distilled TPM | Pre-distilled Topanol A | TPM/Topanol A Distillate |
|----|-------------------|-------------------------|--------------------------|
| Li | 0.06              | 0.01                    | nd                       |
| Na | 8.405             | 389.835                 | 0.08                     |
| Mg | 1.105             | nd                      | nd                       |
| Al | 0.075             | 0.03                    | nd                       |
| K  | 8.075             | 1.34                    | nd                       |
| Ca | 4.555             | 15.785                  | nd                       |
| V  | 0.025             | 0.01                    | nd                       |
| Cr | 0.11              | 0.035                   | nd                       |
| Mn | 1.07              | 0.03                    | nd                       |
| Fe | 22.71             | 3.605                   | nd                       |
| Co | nd                | nd                      | nd                       |
| Ni | nd                | nd                      | nd                       |
| Cu | 0.345             | 2.17                    | nd                       |
| Ti | 1.28              | nd                      | nd                       |
| Zn | 92.835            | 15.5                    | nd                       |
| As | 0.03              | nd                      | nd                       |
| Ag | 0.2               | nd                      | nd                       |
| Cd | nd                | nd                      | nd                       |
| Sn | 0.07              | 0.965                   | nd                       |
| Ba | nd                | nd                      | nd                       |
| W  | 0.075             | nd                      | nd                       |
| Au | 0.23              | nd                      | nd                       |
| Pb | nd                | 0.2                     | nd                       |
| Total | 141.255        | 429.515                 | 0.08                     | nd = below detection limit

Example 4

Figure 2:
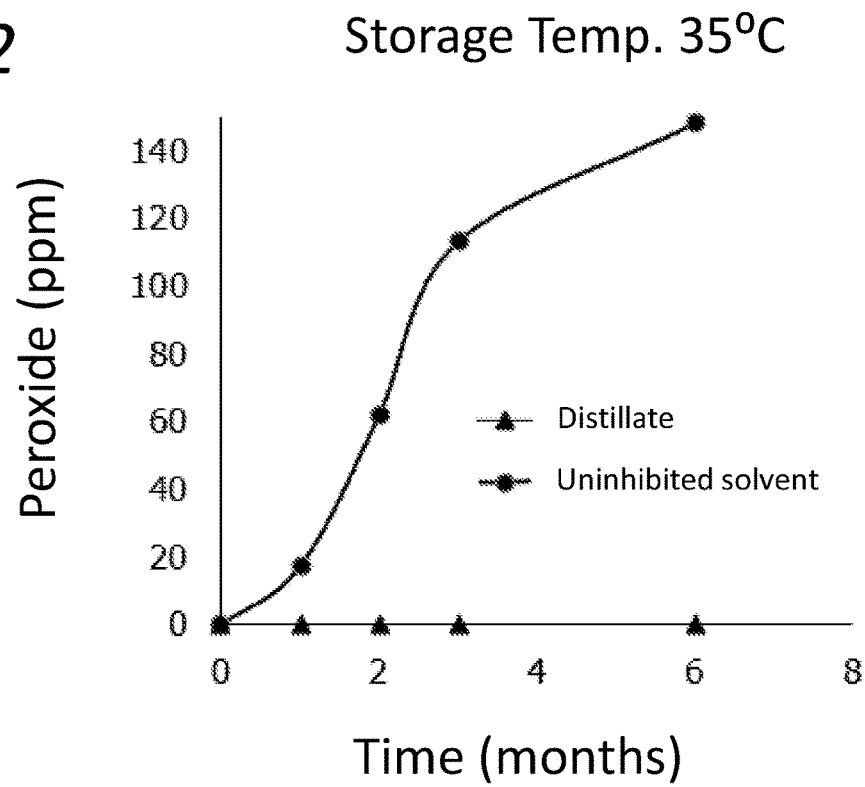
FIG. 2 is a graph showing peroxide content as a function of time at 35° C. for peroxide-inhibited solvent purified in accordance with the invention and for a comparative uninhibited solvent.

Samples of the distillate obtained in Example 3 were placed in two containers and stored at 4° C. and 35° C. Samples of the uninhibited TPM glycol ether were separately placed in two additional containers and stored at 4° C. and 35° C. Samples from the containers were periodically removed from the containers by pipet and analyzed for total peroxide content by redox-potentiometric titration. The results are shown in FIGS. 1-2, showing peroxide content as a function of time at 4° C. and 35° C., for the peroxide-inhibited distillate and the uninhibited solvent.

What is claimed is:

1. A purification method, comprising:
   (a) providing an organic solvent and a phenolic peroxide formation inhibitor, wherein the organic solvent has a first boiling point at standard atmospheric pressure ($bp_1$) and the phenolic peroxide formation inhibitor has a second boiling point at standard atmospheric pressure ($bp_2$) that satisfy the following inequality (I):

$$bp_2 \leq (1.10)(bp_1) \tag{I}$$

and (b) heating the organic solvent and the phenolic peroxide formation inhibitor to a temperature causing the organic solvent and phenolic peroxide formation inhibitor to vaporize, and (ii) condensing the vaporized organic solvent and phenolic peroxide formation inhibitor to provide a purified mixture of the organic solvent and phenolic peroxide formation inhibitor.

2. The purification method of claim 1, wherein the purification method is a distillation process.

3. The purification method of claim 1, wherein the purification method is performed under vacuum.

4. The purification method of claim 1, wherein the organic solvent and the phenolic peroxide formation inhibitor are mixed prior to the step of heating.

5. The purification method of claim 1, wherein the phenolic peroxide formation inhibitor has a second boiling point at standard atmospheric pressure ($bp_2$) that satisfies the following inequality (II):

$$(0.90)(bp_1) < bp_2 < (1.10)(bp_1) \tag{II}$$

6. The purification method claim 1, wherein $bp_2$ is less than $bp_1$.

7. The purification method of claim 1, wherein the phenolic peroxide formation inhibitor is chosen from phenol, 2-methylphenol, 2-(trifluoromethyl)phenol, 4-methoxyphenol, 4-(trifluoromethoxy)phenol, 2,4-dimethyl-6-tert-butylphenol, 2,4-di(trifluoromethyl)-6-tert-butylphenol, 2,6-di-tert-butylphenol, 4-tert-butylpyrocatechol, and combinations thereof.

8. The purification method of claim 7, wherein the phenolic peroxide formation inhibitor is chosen from 2-methylphenol, 2,4-dimethyl-6-tert-butylphenol, and combinations thereof.

9. The purification method of claim 1, wherein the organic solvent is chosen from one or more of isoamyl ether, 2-butoxyethanol, dipropylene glycol monomethyl ether, dipropylene glycol dimethyl ether, tripropylene glycol monomethyl ether, ethyl-3-ethoxy propionate, ethyl lactate, propylene glycol, tripropylene glycol, diisopropyl benzene, triisopropyl benzene, cyclopentanone, cyclohexanone and combinations thereof.

10. The purification method of claim 9, wherein the organic solvent is tripropylene glycol monomethyl ether and the phenolic peroxide formation inhibitor is 2,4-dimethyl-6-tert-butylphenol, or wherein the solvent is dipropylene glycol methyl ether and the phenolic peroxide formation inhibitor is 2-methylphenol.

* * * * *